(12) United States Patent
Adjei et al.

(10) Patent No.: US 6,261,539 B1
(45) Date of Patent: Jul. 17, 2001

(54) MEDICINAL AEROSOL FORMULATION

(76) Inventors: Akwete Adjei, 15 Tillman Ct.;
Anthony J. Cutie, P.O. Box 6725, both of Bridgewater, NJ (US) 08807

( * ) Notice: Subject to any disclaimer, the term of this patent is extended or adjusted under 35 U.S.C. 154(b) by 0 days.

(21) Appl. No.: 09/209,228

(22) Filed: Dec. 10, 1998

(51) Int. Cl.⁷ .................................................... A61K 9/12
(52) U.S. Cl. ................................................. 424/46; 424/45
(58) Field of Search ........................................ 424/45, 46

(56) References Cited

U.S. PATENT DOCUMENTS

| | | | |
|---|---|---|---|
| 4,174,295 | * 11/1979 | Bargigia et al. | 252/305 |
| 5,225,183 | * 7/1993 | Purewal et al. | 424/45 |
| 5,674,472 | * 10/1997 | Akehurst et al. | 424/45 |
| 5,891,420 | * 4/1999 | Cutie | 424/46 |
| 5,916,540 | * 6/1999 | Akehurst et al. | 424/45 |
| 5,955,439 | * 9/1999 | Green | 514/23 |

FOREIGN PATENT DOCUMENTS

0518600 * 12/1992 (EP) .

* cited by examiner

*Primary Examiner*—Thurman K. Page
*Assistant Examiner*—P. E. McQueeney
(74) *Attorney, Agent, or Firm*—Frommer Lawrence & Haug LLP

(57) ABSTRACT

This invention relates to a medicinal aerosol formulation and more particularly, to a medicinal aerosol formulation containing a particulate drug, a propellant and a stabilizing agent comprising a water addition.

34 Claims, No Drawings

MEDICINAL AEROSOL FORMULATION

BACKGROUND OF THE INVENTION

1. Field of the Invention

This invention relates to a medicinal aerosol formulation, and more particularly, to a medicinal aerosol formulation comprising a stabilizer comprising a water addition.

2. Description of the Related Art

Delivery of drugs to the lung by way of inhalation is an important means of treating a variety of conditions, including such common local conditions as bronchial asthma and chronic obstructive pulmonary disease and some systemic conditions, including hormone replacement, pain management, cystic fibrosis, etc. Steroids, β2 agonists, anticholinergic agents, proteins and polypeptides are among the drugs that are administered to the lung for such purposes. Such drugs are commonly administered to the lung in the form of an aerosol of particles of respirable size (less than about 10 μm in diameter). The aerosol formulation can be presented as a liquid or a dry powder. In order to assure proper particle size in a liquid aerosol, as a suspension, particles can be prepared in respirable size and then incorporated into the suspension formulation containing a propellant. Alternatively, formulations can be prepared in solution form in order to avoid the concern for proper particle size in the formulation. Solution formulations must nevertheless be dispensed in a manner that produces particles or droplets of respirable size.

Once prepared an aerosol formulation is filled into an aerosol canister equipped with a metered dose valve. In the hands of the patient the formulation is dispensed via an actuator adapted to direct the dose from the valve to the patient.

It is important that an aerosol formulation be stable such that the pressurized dose discharged from the metered dose valve is reproducible. Rapid creaming, settling, or flocculation after agitation are common sources of dose irreproducibility in suspension formulations. This is especially true where a binary aerosol formulation containing only medicament and propellant, e.g. 1,1,1,2-tetrafluoroethane, is employed or where such formulation contains small amounts of surfactant as well. Sticking of the valve also can cause dose irreproducibility. In order to overcome these problems aerosol formulations often contain surfactants, which serve as suspending aids to stabilize the suspension for a time sufficient to allow for reproducible dosing. Certain surfactants also function as lubricants to lubricate the valve to assure smooth actuation. Myriad materials are known and disclosed for use as dispersing aids in aerosol formulations. Suitability of materials, however, is dependent on the particular drug and the propellant or class of propellant used in the formulation.

It is sometimes difficult to dissolve sufficient quantities of conventional surfactants in hydrofluorocarbon (HFC) propellants such as HFC-134a and HFC-227. Cosolvents, such as ethanol, have been used to overcome this problem, as described in U.S. Pat. No. 5,225,183. An alternative approach that avoids cosolvents involves materials that are soluble in hydrofluorocarbon propellants and are said to be effective surfactants or dispersing aids in an aerosol formulation. Among such materials are certain fluorinated surfactants and certain polyethyoxysurfactants.

It is known in the art that the presence of water in conventional aerosol formulations often result in a number of potential problems, e.g. stability of the formulation, erratic dose delivery, and, in some cases free radical reactions in the propellant. Therefore, it has generally been accepted that these preparations should be maintained substantially free of water. The rigorous exclusion of atmospheric moisture during both the manufacture and storage of such formulations, referred to as "developed" or "nascent" formulation water, increases the difficulties of preparing satisfactory stable aerosols containing the drug and raises the overall cost of the final product, especially when a moisture barrier, e.g. foil pouching, is included as a secondary package.

An exception had been found for beclomethasone dipropionate monohydrate. It has been reported that a formulation of this particular medicament combined with an amount of water in addition to its water of hydration is stable. In this regard, reference is made to U.S. Pat. No. 5,695,744.

What has not been appreciated, however, is that despite all efforts an amount of water develops in medicinal aerosol formulations during processing of such formulations which can not be eliminated and is always present ("developed" or "nascent" formulation water). Most surprising and unexpected is that such unstable formulations, containing nascent formulation water, can be and are stabilized by the presence of a concentration of water added in addition to the nascent or developed formulation water which stabilizes such medicament formulations, and where such concentration of water addition is much less than that required by the beclomethasone dipropionate monohydrate formulations reported in U.S. Pat. No. 5,696,744.

SUMMARY OF THE INVENTION

It has surprisingly been found that novel medicinal aerosol formulations can be obtained without the use of either cosolvents, such as ethanol, or surfactants, such as sorbitan trioleate which are added to a binary aerosol formulation. Stable medicinal aerosol formulations are obtained by the use of a water addition.

DETAILED DESCRIPTION OF THE INVENTION

This invention involves a stable suspension aerosol formulation suitable for pressurized delivery which comprises (1) a particulate medicament or drug, (2) a suitable propellant, and (3) a stabilizer comprising a water addition.

A suitable medicament or drug is one which is suitable for administration by inhalation, the inhalation being used for oral and nasal inhalation therapy. Therapeutic categories of drugs or medicaments include cardiovascular drugs, antiallergics, analgesics, brochodilators, antihistamines, antitussives, antifungals, antivirals, antibiotics, pain medicaments, antiinflammatories, peptides, proteins and steroids.

Particularly suitable medicaments or drugs include albuterol (also known as salbutamol), atropine, budesonide, cromolyn, epinephrine, ephedrine, fentanyl, flunisolide, formoterol, ipratropium bromide, isoproterenol, pirbuterol, prednisolone, triamcinolone acetonide, salmeterol, amiloride, fluticasone, fluticasone esters, such as phosphate, monohydrate and furoate, (−)4-amino-3,5-dichloro-α-[[[6 (2-pyridinyl)ethoxy] hexyl] amino] methyl]benzenemethanol. Also included are the suitable acid addition salts of the foregoing drugs, their hydrates and their other solvates. In this regard, suitable acid addition salts include the salts obtained from inorganic acids, such as hydrochloric, hydrobromic, sulfuric, nitric, phosphoric and perchloric acids as well as organic acids such as tartaric, citric, acetic, succinic, maleic, fumaric and oxalic acids. Suitable pharmaceutically acceptable solvates include solvates with ethylactate, alkanes, ethers, alcohols and water.

For purposes of the formulations of this invention, which are intended for inhalation into the lungs, the medicament or drug is preferably micronized whereby a therapeutically effective amount or fraction (e.g., ninety percent or more) of the drug is particulate. Typically, the particles have a diameter of less than about 10 microns, and preferably less than about 5 microns, in order that the particles can be inhaled into the respiratory tract and/or lungs.

The particulate medicament or drug is present in the inventive formulations in a therapeutically effective amount, that is, an amount such that the drug can be administered as an aerosol, such as topically, or via oral or nasal inhalation, and cause its desired therapeutic effect, typically preferred with one dose, or through several doses. The particulate drug is administered as an aerosol from a conventional valve, e.g., a metered dose valve.

The term "amount" as used herein refers to quantity or to concentration as appropriate to the context. The amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors. Generally a therapeutically effective amount will be from about 0.001 parts by weight to about 2 parts by weight based on 100 parts by weight of the propellant.

A suitable propellant is selected. A suitable propellant is any fluorocarbon, e.g. a 1–4 hydrogen containing flurocarbon(, such as $CHF_2CHF_2$, $CF_3CH_2F$, $CH_2F_2CH_3$ and $CF_3CHFCF_3$)), a perfluorocarbon, e.g. a 1–4 carbon perfluorocarbon, (such as $CF_3CF_3$, $CF_3CF_2CF_3$); or any mixture of the foregoing, having a sufficient vapor pressure to render them effective as propellants. Some typical suitable propellants include conventional chlorofluorocarbon (CFC) propellants such as mixtures of propellants 11, 12 and 114. Non-CFC propellants such as 1,1,1,2-tetrafluoroethane (Propellant 134a), 1,1,1,2,3,3,3-heptafluoropropane (Propellant 227) or mixtures thereof are preferred. The propellant is preferably present in an amount sufficient to propel a plurality of the selected doses of drug from an aerosol canister.

A suitable stabilizer is selected. A suitable stabilizer is a "water addition". As used herein a "water addition" is an amount of water which (1) is added, either initially with other components of the aerosol formulation, e.g. medicament and propellant, or after the other components, e.g. medicament, propellant, are combined and processed, (2) is in addition to the water which is always present and which develops during processing and/or storage of the aerosol formulation, i.e. "developed" or "nascent" formulation water, and (3) is present in an amount which stabilizes the ordinarily unstable medicinal aerosol formulation having nascent formulation water.

An aerosol formulation preferably comprises the water addition in an amount effective to stabilize the formulation relative to an identical formulation not containing the water addition, i.e. containing only nascent formulation water, such that the drug does not settle, cream or flocculate after agitation so quickly as to prevent reproducible dosing of the drug. Reproducible dosing can be achieved if the formulation retains a substantially uniform drug concentration for about two or three seconds after agitation.

The particular amount of the water addition that constitutes an effective amount is dependent upon the particular propellant and on the particular drug used in the formulation. It is therefore not practical to enumerate specific effective amounts for use with specific formulations of the invention, but such amounts can readily be determined by those skilled in the art with due consideration of the factors set forth above. Generally, however, the water addition must be present in a formulation in an amount in excess of the concentration of the nascent formulation water. Such concentration of nascent formulation water typically ranges up to 300 parts by weight per one million parts by weight of the total weight of the aerosol formulation. Accordingly, the water addition in excess of this nascent water concentration typically ranges from about 300 parts by weight to 2000 parts by weight per one million parts by weight of the total aerosol formulation weight. Most preferred is that the concentration of the water addition is from 500 parts by weight to 700 parts by weight per one million parts by weight of the total weight of the medicinal aerosol formulation.

It is to be emphasized that this is an amount which exceeds the amount of nascent or developed formulation water. It is also to be stressed that this amount of water addition can be added and initially combined with the other components of the formulation, e.g. medicament, such as triamcinolone acetonide, and propellant, e.g. 1,1,1,2-tetrahydrofluoroehtane, or added to the resultant formulation after these other components have been processed, e.g. prior to or subsequent to storage.

It has surprisingly been found that the formulation of the invention is stable without the necessity of employing a cosolvent, such as ethanol, or surfactants. However, further components, such as conventional lubricants or surfactants, cosolvents, ethanol, etc., can also be present in an aerosol formulation of the invention in suitable amounts readily determined by those skilled in the art. In this regard, reference is made to U.S. Pat. No. 5,225,183, which is incorporated by reference hereinto in its entirety.

A most preferred formulation comprises the medicament, the propellant, the ethanol cosolvent and the water addition, for example, triamcinolone acetonide, 1,1,1,2-tetrafluoroethane, ethanol and the water addition.

Generally the formulations of the invention can be prepared by combining (i) the drug in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular stabilizer and other adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations of the invention are preferably dispensed via a valve assembly wherein the diaphragm is made of a nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS 1085 NT polyolefin (Union Carbide).

Conventional aerosol canisters, coated or uncoated, anodized or unanodized, e.g., those of aluminum, glass, stainless steel, polyethylene terephthalate, and coated canisters or cans with epon, epoxy, etc., can be used to contain a formulation of the invention.

The formulation of the invention can be delivered to the respiratory tract and/or lung by oral inhalation in order to effect bronchodilation or in order to treat a condition susceptible of treatment by inhalation, e.g., asthma, chronic obstructive pulmonary disease. The formulations of the invention can also be delivered by nasal inhalation in order to treat, e.g., allergic rhinitis, rhinitis, (local) or diabetes (systemic), or they can be delivered via topical (e.g., buccal) administration in order to treat, e.g., angina or local infection.

What is claimed is:

1. A medicinal aerosol formulation, which consists essentially of:
   (a) a therapeutically effective amount of a particulate medicament;
   (b) a propellant; and
   (c) a stabilizer consisting of water, in addition to nascent water present in formulation, in an amount ranging from about 300 parts by weight to about 2000 parts by weight to one million parts by total weight of the formulation;
   which is obtained by
   (a) either:
      i.) combining said medicament, propellant and water; or
      ii) combining said medicament and propellant followed by the addition of water; and
   (b) dispersing the medicament propellant and water.

2. The formulation as defined in claim 1, wherein the medicament is selected form the group consisting of albuterol, atropine, budesonide, cromolyn, epinephrine, ephedrine, fentanyl, flunisolide, formoterol, ipratropium bromide, isoproterenol, pirbuterol, prednisone, triamcinolone acetonide, salmeterol, amiloride, fluticasone, (−)4-amino-3,5-dichloro-α-[[[6(2-pyridinyl)ethoxy] hexyl] amino] methyl]benzene-methanol and pharmaceutically acceptable esters and solvates of the foregoing.

3. The formulation as defined in claim 2 wherein the medicament is budesonide, formoterol or fluticasone.

4. The formulation in claim 1, wherein the medicament is fluticasone.

5. The formulation in claim 1, wherein the medicament to are fluticasone and an anticholinergic agent.

6. The formulation as defined in claim 1, wherein said propellant is selected from the group consisting of 1,1,1,2-tetrafluoroethane, 1,1,1,2,3,3,3-heptafluoropropane or a mixture thereof.

7. The formulation as defined in claim 1 wherein said stabilizer is present in an amount ranging from about 500 parts by weight to about 2000 parts weight based on 1 million parts by total weight of the formulation.

8. The formulation as defined in claim 7 wherein said stabilizer is present in an amount ranging from 500 parts by weight to 700 parts by weight to one million parts by total weight of the formulation.

9. A formulation according to claim 1 in an aerosol canister equipped with a metered dose valve.

10. A method of treating in an animal a condition capable of treatment by oral or nasal inhalation, which comprises, administering a formulation according to claim 1 to said animal by oral or nasal inhalation.

11. A metered dose inhaler containing a medicinal aerosol formulation, wherein the medicinal aerosol formulation is as defined in claim 1.

12. The metered dose inhaler as defined in claim 11, wherein the medicament is fluticasone or fluticasone and an anticholinergic agent.

13. The metered dose inhaler as defined in claim 11 wherein the medicament is selected from the group consisting of albuterol, atropine, budesonide, cromolyn, epinephrine, ephedrine, fentanyl, flunisolide, formoterol, ipratropium bromide, isoproterenol, pirbuterol, prednisone, triamcinolone acetonide, salmeterol, amiloride, fluticasone, an ester of fluticasone,(−)4-amino-3,5-dichloro-α-[[[6(2-pyridinyl)ethoxy] hexyl] amino] methyl]benzene-methanol and pharmaceutically acceptable hydrates, salts and solvates of the foregoing.

14. The metered dose inhaler as defined in claim 13 wherein the propellant is selected from the group consisting of 1,1,1,2-tetrafluoroethane, 1,1,1,2,3,3,3-heptafluoropropane or a mixture thereof.

15. The metered dose inhaler as defined in claim 14 wherein said medicament comprises triamcinolone acetonide.

16. The metered dose inhaler as defined in claim 15 wherein said stabilizer is present in an amount ranging from 500 parts by weight to 700 parts by weight per one million parts by weight of the medicinal aerosol formulation.

17. A medicinal aerosol formulation, which consists essentially of:
   (a) a therapeutically effective amount of a particulate medicament;
   (b) a propellant;
   (c) a cosolvent; and
   (d) a stabilizer consisting of water, in addition to nascent water present in formulation, in an amount ranging from about 300 parts by weight to about 2000 parts by weight to one million parts by total weight of the formulation;
   which is obtained by
   (a) either:
      i.) combining said medicament, propellant, cosolvent and water; or
      ii) combining said medicament, propellant, and cosolvent followed by the addition of water; and
   (b) dispersing the medicament propellant, cosolvent and water.

18. The formulation as defined in claim 17 wherein said medicament is selected from the group consisting of albuterol, atropine, budesonide, cromolyn, epinephrine, ephedrine, fentanyl, flunisolide, formoterol, ipratropium bromide, isoproterenol, pirbuterol, prednisone, triamcinolone acetonide, salmeterol, amiloride, fluticasone, (−)4- amino-3,5-dichloro-α-[[[6(2-pyridinyl)ethoxy] hexyl] amino] methyl]benzene-methanol and pharmaceutically acceptable salts, esters, hydrates and solvates of the foregoing.

19. The formulation as defined in claim 17 wherein said medicament is selected from the group consisting of albuterol, atropine, budesonide, cromolyn, epinephrine, ephedrine, fentanyl, flunisolide, formoterol, ipratropium bromide, isoproterenol, pirbuterol, prednisone, triamcinolone acetonide, salmeterol, amiloride, fluticasone, (−)4-amino-3,5-dichloro-α-[[[6(2-pyridinyl)ethoxy] hexyl] amino] methyl]benzene-methanol and pharmaceutically acceptable esters and solvates of the foregoing.

20. The formulation as defined in claim 17 wherein said medicament comprises triamcinolone acetonide, budesonide, fomoterol, or fluticasone.

21. The formulation as defined in claim 17 wherein said cosolvent is ethanol.

22. The formulation as defined in claim 17 wherein said stabilizer is present in an amount ranging from about 500 parts by weight to about 2000 parts weight based on 1 million parts by total weight of the formulation.

23. The formulation as defined in claim 17 wherein said stabilizer is present in an amount ranging from 500 parts by weight to 700 parts by weight to one million parts by total weight of the formulation.

24. A method of treating in an animal a condition capable of treatment by oral or nasal inhalation, which comprises, administering a formulation according to claim 17 to said animal by oral or nasal inhalation.

25. A formulation according to claim 17 in an aerosol canister equipped with a metered dose valve.

26. A metered dose inhaler containing a medicinal aerosol formulation, wherein the medicinal aerosol formulation is as defined in claim 17.

27. The metered dose inhaler as defined in claim 26 wherein the drug is selected from the group consisting of albuterol, atropine, budesonide, cromolyn, epinephrine, ephedrine, fentanyl, flunisolide, formoterol, ipratropium bromide, isoproterenol, pirbuterol, prednisone, triamcinolone acetonide, salmeterol, amiloride, fluticasone, (−)4-amino-3,5-dichloro-α-[[[6(2-pyridinyl)ethoxy] hexyl] amino] methyl]benzene-methanol and pharmaceutically acceptable hydrates, salts and solvates of the foregoing.

28. The metered dose inhaler as defined in claim 27 wherein the propellant is selected from the group consisting of 1,1,1,2-tetrafluoroethane, 1,1,1,2,3,3,3-heptafluoropropane or a mixture thereof.

29. The metered dose inhaler as defined in claim 28 wherein said medicament triamcinolone acetonide, budesonide, budesonide, or fluticasone, and the cosolvent is ethanol.

30. The metered dose inhaler as defined in claim 29 wherein said stabilizer is present in an amount ranging from 500 parts by weight to 700 parts by weight per one million parts by weight of the medicinal aerosol formulation.

31. A medicinal aerosol formulation, which consists essentially of:
    (a) a therapeutically effective amount of a particulate medicament;
    (b) a propellant;
    (c) optionally, a cosolvent; and
    (d) a stabilizer consisting of water, in addition to nascent water present in formulation, in an amount ranging from about 300 parts by weight to about 2000 parts by weight to one million parts by total weight of the formulation.

32. A medicinal aerosol formulation as defined in claim 31, wherein the medicament is selected from the group consisting of albuterol, atropine, budesonide, cromolyn, epinephrine, ephedrine, fentanyl, flunisolide, formoterol, ipratropium bromide, isoproterenol, pirbuterol, prednisone, triamcinolone acetonide, salmeterol, amiloride, fluticasone, (−)4-amino-3,5-dichloroα-[[[6(2-pyridinyl)ethoxy] hexyl] amino] methyl]benzene-methanol and pharmaceutically acceptable, salts, esters, hydrates and solvates of the foregoing and the propellent is selected from the group consisting of 1,1,1,2-tetrafluoroethane, 1,1,1,2,3,3,3-heptafluoropropane or a mixture thereof.

33. The formulation as defined in claim 32 wherein a cosolvent is present.

34. The formulation as defined in claim 32, wherein the medicament is triamcinolone acetonide, budesonide, formoterol or fluticasone.

* * * * *